(12) United States Patent
Cabuz et al.

(10) Patent No.: US 6,549,275 B1
(45) Date of Patent: Apr. 15, 2003

(54) OPTICAL DETECTION SYSTEM FOR FLOW CYTOMETRY

(75) Inventors: Cleopatra Cabuz, Edina, MN (US); J. David Zook, Golden Valley, MN (US); James Allen Cox, New Brighton, MN (US); Aravind Padmanabhan, Plymouth, MN (US); Teresa M. Marta, White Bear Lake, MN (US)

(73) Assignee: Honeywell International Inc., Morristown, NJ (US)

(*) Notice: Subject to any disclaimer, the term of this patent is extended or adjusted under 35 U.S.C. 154(b) by 0 days.

(21) Appl. No.: 09/630,927

(22) Filed: Aug. 2, 2000

(51) Int. Cl.[7] ............................................. G01N 33/48
(52) U.S. Cl. .................................................... 356/39
(58) Field of Search ............................ 356/39, 317, 411; 250/461.2, 358.2, 226

(56) References Cited

U.S. PATENT DOCUMENTS

| | | | | |
|---|---|---|---|---|
| 3,976,862 A | * | 8/1976 | Curbelo | 235/151.34 |
| 4,478,076 A | | 10/1984 | Bohrer | 73/204 |
| 4,478,077 A | | 10/1984 | Boher | 73/204 |
| 4,501,144 A | | 2/1985 | Higashi et al. | 73/204 |
| 4,651,564 A | | 3/1987 | Johnson et al. | 73/204 |
| 4,683,159 A | | 7/1987 | Bohrer et al. | 428/138 |
| 4,745,279 A | * | 5/1988 | Karkar et al. | 250/343 |
| 4,874,949 A | * | 10/1989 | Harris et al. | 250/343 |
| 5,050,429 A | | 9/1991 | Nishimoto et al. | 73/204.26 |
| 5,082,242 A | | 1/1992 | Bonne et al. | 251/129.01 |
| 5,108,623 A | | 4/1992 | Cangelosi et al. | 210/744 |
| 5,176,358 A | | 1/1993 | Bonne et al. | 251/30.05 |
| 5,185,641 A | * | 2/1993 | Igushi et al. | 356/336 |
| 5,244,537 A | | 9/1993 | Ohnstein | 156/643 |
| 5,323,999 A | | 6/1994 | Bonne et al. | 251/11 |
| 5,441,597 A | | 8/1995 | Bonne et al. | 216/2 |
| 5,528,045 A | * | 6/1996 | Hoffman et al. | 250/458.1 |
| 5,601,080 A | * | 2/1997 | Oppenheimer | 128/633 |
| 5,633,724 A | * | 5/1997 | King et al. | 356/445 |
| 5,683,159 A | | 11/1997 | Johnson | 312/334.7 |
| 5,716,852 A | | 2/1998 | Yager et al. | 436/172 |
| 5,726,751 A | | 3/1998 | Altendorf et al. | 356/246 |
| 5,793,485 A | | 8/1998 | Gourley | 356/318 |
| 5,799,030 A | | 8/1998 | Brenner | 372/50 |
| 5,822,170 A | | 10/1998 | Cabuz et al. | 361/225 |
| 5,836,750 A | | 11/1998 | Cabuz | 417/322 |
| 5,880,474 A | * | 3/1999 | Norton et al. | 250/458.1 |
| 5,893,722 A | | 4/1999 | Hibbs-Brenner et al. | 438/45 |
| 5,922,210 A | | 7/1999 | Brody et al. | 210/767 |
| 5,932,100 A | | 8/1999 | Yager et al. | 210/634 |
| 5,948,684 A | | 9/1999 | Weigl et al. | 436/52 |
| 5,971,158 A | | 10/1999 | Yager et al. | 209/155 |
| 5,972,710 A | | 10/1999 | Weigl et al. | 436/34 |
| 5,974,867 A | | 11/1999 | Forster et al. | 73/61.41 |
| 6,007,775 A | | 12/1999 | Yager | 422/57 |
| 6,139,800 A | * | 10/2000 | Chandler | 422/82.08 |
| 6,249,341 B1 | * | 6/2001 | Basiji et al. | 356/73 |

OTHER PUBLICATIONS http://www.micronics.net/tsensor.htm, pp. 1–4, downloaded Jun. 14, 2000.
http://www.micronics.net/hfilter.htm, pp. 1–3, downloaded Jun. 14, 2000.

(List continued on next page.)

Primary Examiner—Michael P. Stafira
(74) Attorney, Agent, or Firm—Crompton Seagar & Tufte; Andrew A. Abeyta

(57) ABSTRACT

An optical detection system for flow cytometry that uses two or more light sources positioned laterally at different distances from the central axis of the flow stream for providing light through different parts of the flow stream. By using two or more light sources, the particle position can be detected, and the alignment and width of the core stream can be monitored and controlled. In addition, the velocity and size of the particles can be more accurately determined than when only a single light source is used.

43 Claims, 13 Drawing Sheets

OTHER PUBLICATIONS

*http://www.micronics.net/mcytometry.htm*, pp. 1–4, downloaded Jun. 14, 2000.

*http://www.micronics.net/orcafluidics.htm*, pp. 1–4, downloaded Jun. 14, 2000.

Eric Alterndorf et al., "Results Obtained Using a Prototype Microfluidics–Based Hematology Analyzer", Department of Bioengineering, University of Washington, Box 352141, Seattle, WA 98195, dated prior to Aug. 2, 2000, pp. 73–76.

Shapiro, "Practical Flow Cytometry", third edition, 1995, p. 237.

Cleopatra Cabuz et al., "Mesoscopic Sampler Based on 3D Array of Electrostatically Activated Diaphragms", The $10^{th}$ Int. Conf. On Solid–State Sensors and Actuators, Transducers'99, Jun. 7–12, 1999, Sendai Japan, pg. 1890–1.

T. Ohnstein et al., "Micromachined Silicon Microvalve", Proceedings of MEMS, 1990, IEEE Micro Electromechanical Systems, Napa Valley, California, Feb. 11–14, 1990, pp. 95–98.

Strzelecka, E. et al., "Parallel Free–Space Optical Interconnect Based on Arrays of Vertical–Cavity Lasers and Detectors with Monolithic Microlenses", Applied Optics, v. 37(14), May 10, 1998, pp. 2811–21. Copyright 1998 Optical Society of America.

Lehman, J. et al., "High–Frequency Modulation Characteristics of Red VCSELs", Electronics Letters, Feb. 13, 1997, vol. 33(4), pp. 298–300. Copyright 1997 IEE.

"Applying Microfluidic Chemical Analytical Systems To Imperfect Samples", P. Yager et al., Micro Total Analysis Systems 98, D. Harrison & A. van den Berg (ed.), Kluwer Academic Publishers, Dordrecht, 207–212, 1998.

"Design Of Microfluidic Sample Preconditioning Systems For Detection Of Biological Agents In Environmental Samples", Yager, M. et al., SPIE Proceedings, 3515, 252–259, 1998.

"Development Of A Flow Cytometry Based Miniature Chemical Fluid Analysis System Using Fluorscent Microbeads", M. Huang. et al., SPIE Biomedical Optics, BIOS 97, conference proceedings, 1997.

"Differential Blood Cell Counts Obtained Using A Microchannel Based Flow Cytometer", E. Altendorf et al., Solid State Sensors & Actuators, vol. 1, 531, 1997.

"Diffusion–Based Optical Chemical Detection In Silicon Flow Structures", B. Weigl et al., Analytical Methods & Instrumentation, $\mu$TTAS 96 special edition, 1996.

"Fluorescence Analyte Sensing In Whole Blood Based On Diffusion Separation In Silicon–Microfabricated Flow Structures", B. Welgl et al., SPIE Proceedings, J. Lakowitz (ed.), Fluorescence Sensing Technology III, 1997.

"Fluorescence And Absorbance Analyte Sensing In Whole Blood And Plasma Based On Diffusion Separation In Silicon–Microfabricated Flow Structures (T–Sensors™)", B. Weigl, et al., Biomedical Optics, vol. 6, No. 1, Jul. 1997.

"Implementation Of Novel Optical Detection Methods For Clinically Important Blood Analytes Using Microfabricated Flow Structures (T–Sensors™)", E. Altendorf & B. Weigl, MicroTAS 98, Banff, Canada, Apr. 1998.

"Integration Of Microelectrodes With Etched Microchannels For In–Stream Electrochemical Analysis", R.Darling et al., MicroTAS 98, Banff, Canada, Apr. 1998.

"Microfabrication Technology For Research And Diagnostics, Silicon Microchannel Optical Flow Cytometry", E. Altendorf et al., SPIE Proceedings, Biomedical Optics 96, Jan. 1996.

"Microfluidic Approaches To Immunoassays", A. Hatch et al., SPIE conference on Micromachining and Microfabrication Symposium at Santa Clara, CA, Sep. 20–22, 1999.

"Microfluidic Diffusion Based Electrochemical Detection Using Microfabricated Flow Structures (T–Sensors™)", B. Weigl, Analytical Chemistry, submitted 1999.

"Microfluidic Diffusion Based Separation And Detection", B. Weigl, P. Yager, Science, vol. 283, pp 346–7, Jan. 15, 1999.

"Optical And Electrochemical Diffusion–Based Detection Of Analytes In Complex Samples Using Microfabricated Flow Structures (T–SensorSTM)", B. Weigl, R. Darling, P. Yager, J. Kriebel & K. Mayes, Micro– and nanofabn'cated electro–optical mechanical systems for biomedical and environmental applications II–SPIE vol. 3606, Jan. 25–26, 1999.

"Rapid Sequential Chemical Analysis Using Multiple Fluorescent Reporter Beads", B. Weigl et al., $\mu$TTAS 96 Conference Proceedings, 1996.

"Results Obtained Using A Prototype Microfluidics–Based Hematology Analyzer", E.Altendorf et al., SPIE Biomedical Optics 97, 1997.

"Silicon–Microfabricated Diffusion–Based Optical Chemical Sensor", B. Weigh & P. Yager, Reprint from "Sensors & Actuators" B 38–39, 452–457, 1997.

"Simultaneous Self–Referencing Analyte Determination In Complex Sample Solutions Using Microfabricated Flow Structures (T–Sensors™)", B. Weigl et al., Proceedings of MicroTAS 98, 81–4, Banff, Canada, 1998.

"Whole Blood Assays Using Microfluidics–Based T–SensorSTm Technology", B. Weigl, Medical Design Online, *http://news.medicaldesignonline.com/featuresarticles/19990416–5922.html*, Apr. 1999.

* cited by examiner

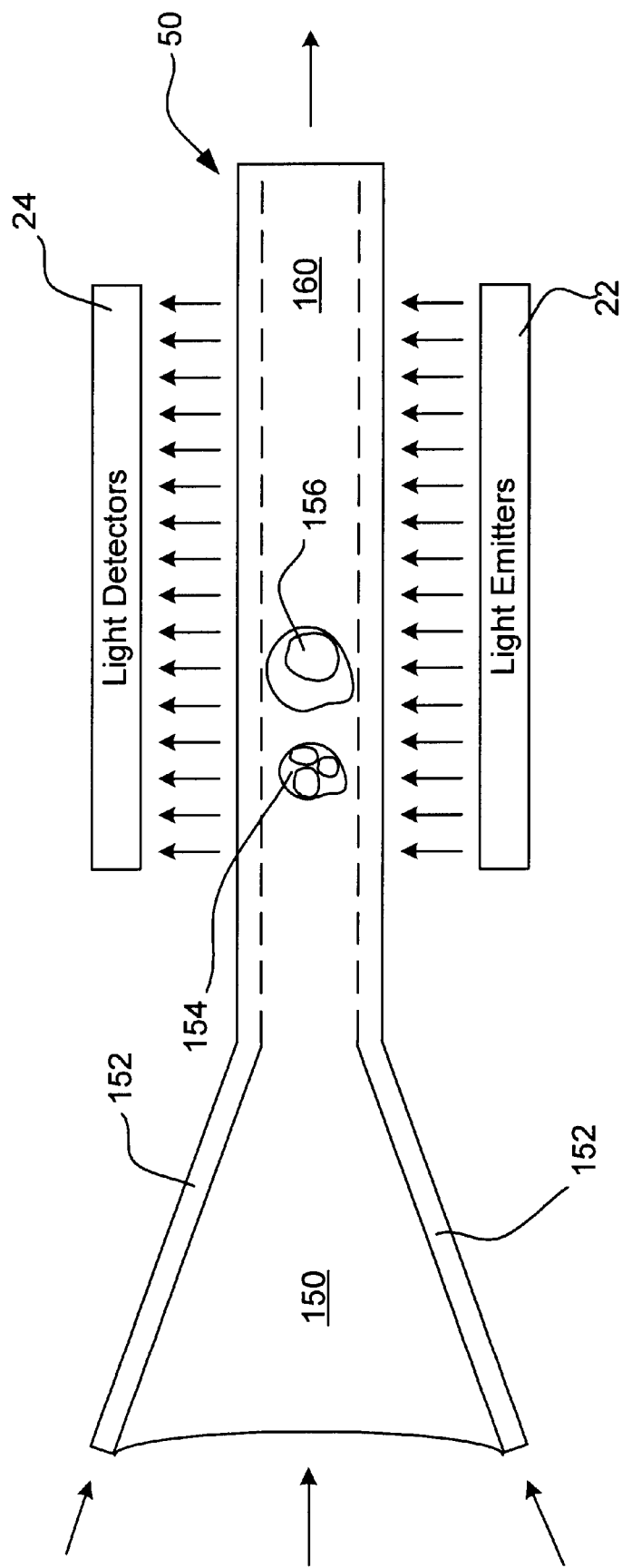

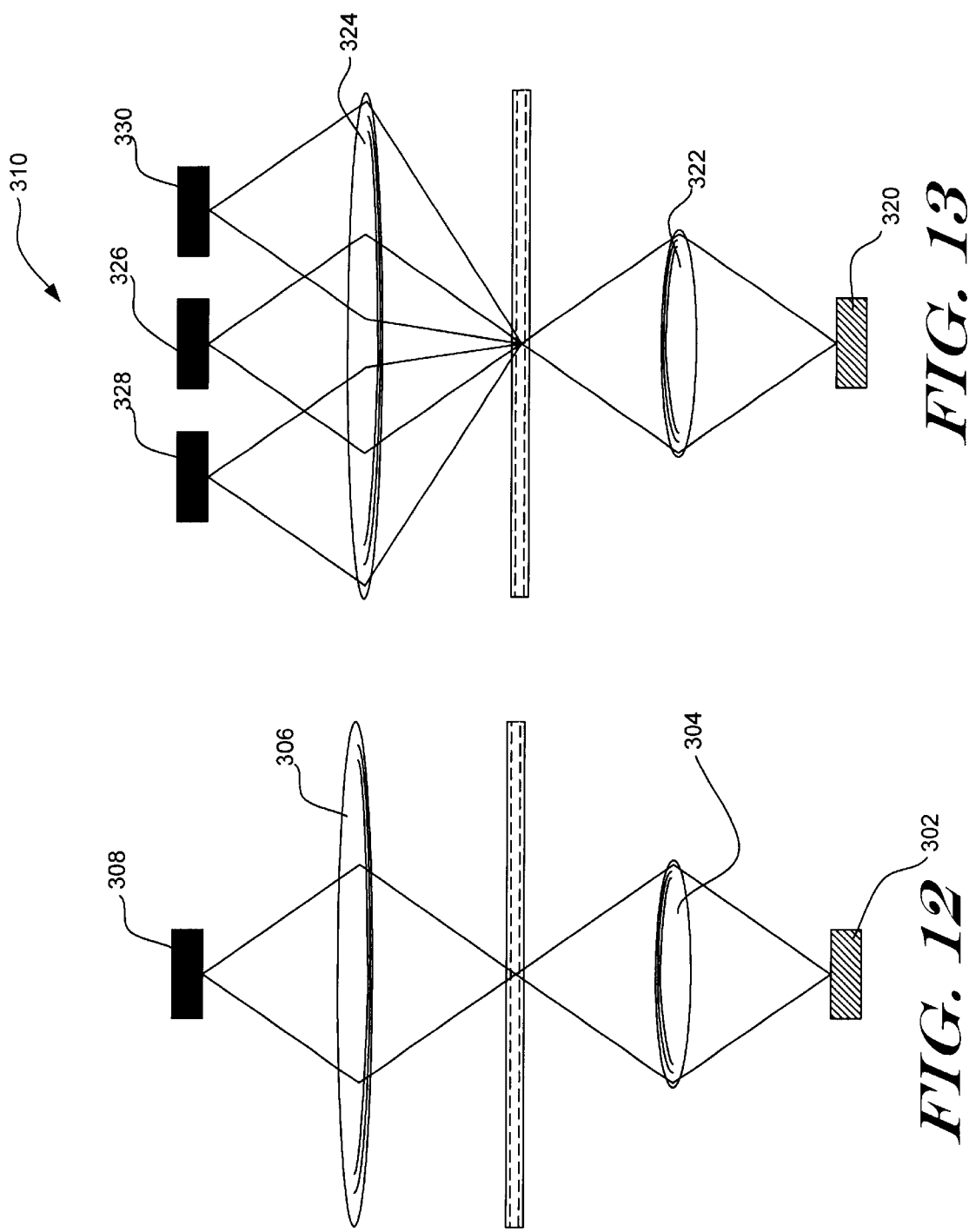

OPTICAL DETECTION SYSTEM FOR FLOW CYTOMETRY

CROSS-REFERENCE TO RELATED CO-PENDING APPLICATIONS

This application is related to co-pending U.S. patent application Ser. No. 09/630,923 to Cabuz et al., filed Aug. 2, 2000, and entitled "FLUID DRIVING SYSTEM FOR FLOW CYTOMETRY", U.S. patent application Ser. No. 09/630,924 to Cabuz et al., filed Aug. 2, 2000, and entitled "PORTABLE FLOW CYTOMETER", and U.S. patent application Ser. No. 09/404,560, filed Sep. 23, 1999, and entitled "ADDRESSABLE VALVE ARRAYS FOR PROPORTIONAL PRESSURE OR FLOW CONTROL", all of which are incorporated herein by reference.

FIELD OF THE INVENTION

The present invention relates generally to flow cytometers. More particularly, the present invention relates to optical detection systems for flow cytometer systems.

BACKGROUND OF THE INVENTION

Flow cytometry is a technique that is used to determine certain physical and chemical properties of microscopic biological particles by sensing certain optical properties of the particles. Flow cytometry is currently used in a wide variety of applications including hematology, immunology, genetics, food science, pharmacology, microbiology, parasitology and oncology.

In flow cytometry, the microscopic biological particles of a sample fluid are arranged in single file in a core stream, typically using hydrodynamic focussing. The particles are then individually interrogated by an optical detection system. The optical detection system provides a light beam, which is scattered by each particle to produce a scatter profile. The scatter profile is analyzed by measuring the light intensity at both small and larger scatter angles. Certain physical and/or chemical properties of each particle can then be determined from the scatter profile.

Conventional cytometer systems use a single light source such as a laser to interrogate each particle. The light beam is often focussed to an elongated shape that covers the uncertainty in particle position due to misalignment and variations in the width of the core stream. A limitation of using a single light source is that the particle position and variations in the width of the core stream cannot be directly detected. Misaligmnents in particle position and variations in the width of the core stream can be indicators of improper core formation. Because there may be no direct way of monitoring the characteristics of the core stream, improper core formation may go undetected.

This limitation may be further compounded because the single laser source configuration often does not provide a constant illumination intensity across the flow channel. As such, particles that pass more toward the edge of the core stream may not be as illuminated as particles that pass near the center. As a result, the sensitivity and accuracy of the system may vary depending on the lateral position of the particle through the focused elongated shape beam. Since there may be no easy way of detecting the lateral position of each particle, the variations in sensitivity and accuracy may go undetected.

Another limitation of using a single light source is that the velocity of each particle cannot be directly determined. Particle velocity is often an important parameter in estimating the particle size from light scatter signals. In conventional flow cytometry systems, the velocity of each particle is extrapolated from the pump flow rates. Accordingly, to accurately gauge the velocity of each particle, the pumps must be very precise, the tolerance of the cytometer flow chambers must be tightly controlled, no fluid failures such as leaks can occur, and no obstructions such as microbubbles can be introduced to disturb the flow or core formation. Satisfying these constraints can add significant complexity and cost to the flow cytometer system.

SUMMARY OF THE INVENTION

The present invention overcomes many of the disadvantages of the prior art by providing an optical detection system that uses two or more light sources positioned laterally at different distances from the central axis of the flow stream for providing light through different parts of the flow stream. By using two or more light sources, the particle position can be detected, and the alignment and width of the core stream can be monitored and controlled. In addition, the velocity and size of the particles can be more accurately determined than in single light source systems.

In one illustrative embodiment of the present invention, a linear array of first light sources that extend along a first light source axis are provided. The first light source axis is rotated relative to the central axis of the flow stream. A lens is provided adjacent each light source to focus the light at the particles in the core stream. A first set of light detectors are placed in-line with each of the first light sources.

Such an arrangement can be used to determine, for example, the lateral position of each of the particles in the core stream, and the alignment and width of the core stream within the overall flow stream. If the core stream of particles has an improper width or is not in proper alignment, a controller can be used to adjust the fluid velocity of the sample fluid or one of the supporting fluids to adjust the width of the core stream or bring the core stream into alignment. The first set of light detectors may also be used to detect the time-of-flight or velocity of each particle, the size of each particle, as well as the number of particles that flow by the detector.

A second set of the light sources may also be provided along a second light source axis. A lens may be provided adjacent each light source to focus the light at the particles in the core stream. A second set of light detectors may then be placed on either side of the in-line position of each light source for measuring the small angle scattering (SALS) produced by selected particles in the flow stream. The second set of light sources may also be used in conjunction with the first set of light sources to determine the time-of-flight or velocity of the particles in the flow stream. By knowing the velocity of the particles, small variations in the flow rate caused by the fluid driver can be minimized or removed by the controller.

A third set of light sources may be provided along a third light source axis. A lens may be provided adjacent each light source to provide collimated light to the flow stream. Annular light detectors may then be placed opposite the light sources for measuring the forward angle scattering (FALS) produced by the selected particles in the flow stream.

The optical detection system of the present invention may be used in conjunction with a portable cytometer system for detecting, for example, neutrophils and/or lymphocytes white blood cells in a blood sample. By examining the scatter profile of each of the particles, the portable cytometer may identify and count the neutrophils and lymphocytes in the blood sample, and provide a clear infection warning with differentiation between viral and bacterial causes.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein:

FIG. 7 is a schematic diagram showing the formation of a flow stream by the hydrodynamic focusing block 88 of FIG. 3;

FIG. 12 is a schematic diagram showing an illustrative light source and detector pair of the first array shown in FIG. 11;

FIG. 13 is a schematic diagram showing an illustrative light source and detector pair of the second array shown in FIG. 11;

DETAILED DESCRIPTION OF THE PREFERRED EMBODIMENTS

Figure 1:
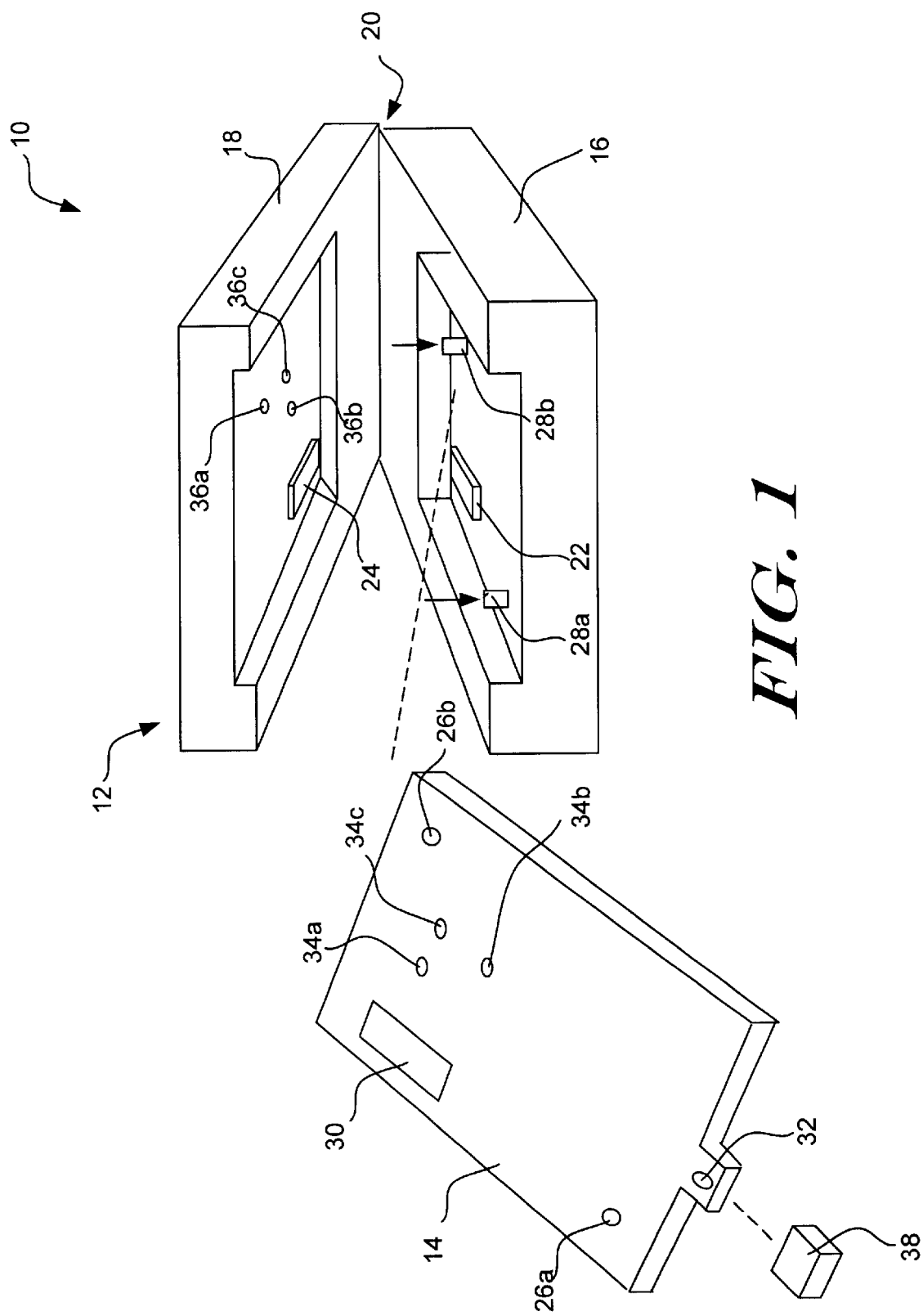
FIG. 1 is a perspective view of an illustrative portable cytometer in accordance with the present invention.

FIG. 1 is a perspective view of an illustrative portable cytometer in accordance with the present invention. The portable cytometer is generally shown at 10, and includes a housing 12 and a removable or replaceable cartridge 14. The illustrative housing 12 includes a base 16, a cover 18, and a hinge 20 that attaches the base 16 to the cover 18. The base 16 includes an array of light sources 22, associated optics and the necessary electronics for operation of the cytometer. The cover 12 includes a manual pressurizing element, pressure-chambers with control microvalves, and an array of light detectors 24 with associated optics.

The removable cartridge 14 preferably receives a sample fluid via a sample collector port 32. A cap 38 may be used to protect the sample collector port 32 when the removable cartridge 14 is not in use. The removable cartridge 14 preferably performs blood dilution, red cell lysing, and hydrodynamic focusing for core formation. The removable cartridge 14 may be constructed similar to the fluidic circuits available from Micronics Technologies, some of which are fabricated using a laminated structure with etched channels.

The removable cartridge 14 is inserted into the housing when the cover 18 is in the open position. The removable cartridge 14 may include holes 26a and 26b for receiving registration pins 28a and 28b in the base 16, which help provide alignment and coupling between the different parts of the instrument. The removable cartridge 14 also preferably includes a transparent flow stream window 30, which is in alignment with the array of the light sources 22 and light detectors 24. When the cover is moved to the closed position, and the system is pressurized, the cover 18 provides controlled pressures to pressure receiving ports 34a, 34b, and 34c in the removable cartridge 14 via pressure providing ports 36a, 36b and 36c, respectively.

To initiate a test, the cover 18 is lifted and a new cartridge 14 is placed and registered onto the base 16. A blood sample is introduced into the sample collector 32. The cover 18 is closed and the system is manually pressurized. Once pressurized, the instrument performs a white blood cell cytometry measurement. The removable cartridge 14 provides blood dilution, red cell lysing, and hydrodynamic focusing for core formation. The light sources 22, light detectors 24 and associated control and processing electronics perform differentiation and counting of white blood cells based on light scattering signals. Rather than using a hinged construction for the housing 12, it is contemplated that a sliding cartridge slot or any other suitable construction may be used.

Figure 2:
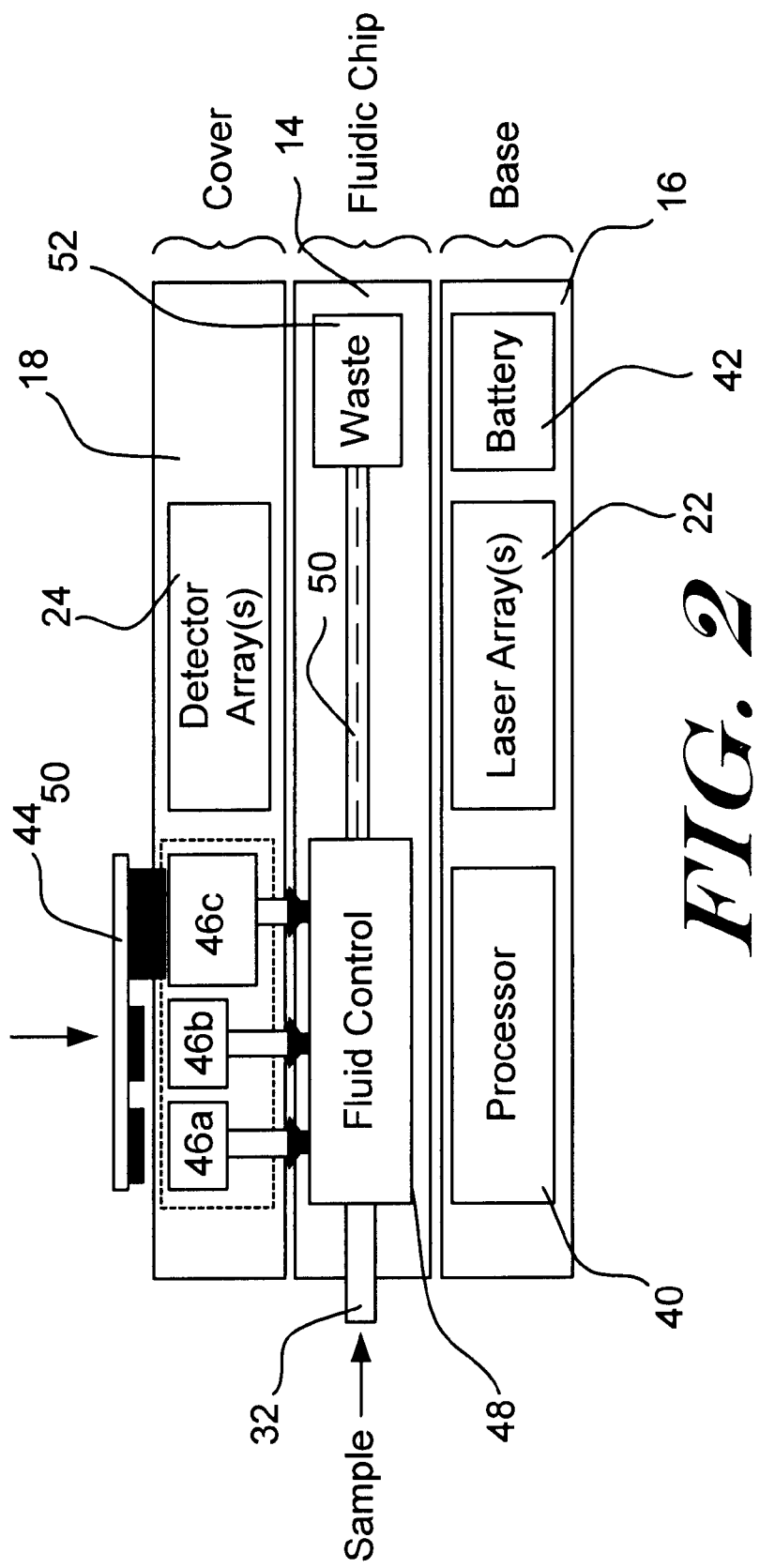
FIG. 2 is a schematic view of the illustrative portable cytometer of FIG. 1.

FIG. 2 is a schematic view of the illustrative portable cytometer of FIG. 1. As above, the base 16 may include an array of light sources 22, associated optics and the necessary control and processing electronics 40 for operation of the cytometer. The base 16 may also include a battery 42 for powering the cytometer. The cover 12 is shown having a manual pressurizing element 44, pressure-chambers 46a, 46b and 46c with control microvalves, and an array of light detectors 24 with associated optics.

The removable cartridge 14 may receive a sample fluid via the sample collector port 32. When pressurized by the cover 18, the removable cartridge 14 performs blood dilution, red cell lysing, and hydrodynamic focusing for core formation in a preferred embodiment. Once formed, the core is provided down a flow stream path 50, which passes the flow stream window 30 of FIG. 1. The array of light sources 22 and associated optics in the base provide light through the core stream via the flow stream window 30. The array of light detectors and associated optics receive scattered and non-scattered light from the core, also via the flow stream window 30. The controller or processor 40 receives output signals from the array of detectors, and differentiates and counts selected white blood cells that are present in the core stream.

It is contemplated that the removable cartridge 14 may include a fluid control block 48 for helping control the velocity of each of the fluids. In the illustrative embodiment, the fluid control block 48 includes flow sensors for sensing the velocity of the various fluids and report the velocities to the controller or processor 40. The controller or processor 40 may then adjust the microvalves associated with pressure-chambers 46a, 46b and 46c to achieve the desired pressures and thus desired fluid velocities for proper operation of the cytometer.

Because blood and other biological waste can spread disease, the removable cartridge 14 preferably has a waste reservoir 52 downstream of the flow stream window 30. The waste reservoir 52 receives and stores the fluid of the flow stream in the removable cartridge 14. When a test is completed, the removable cartridge may be removed and disposed of, preferably in a container compatible with biological waste.

Figure 3:
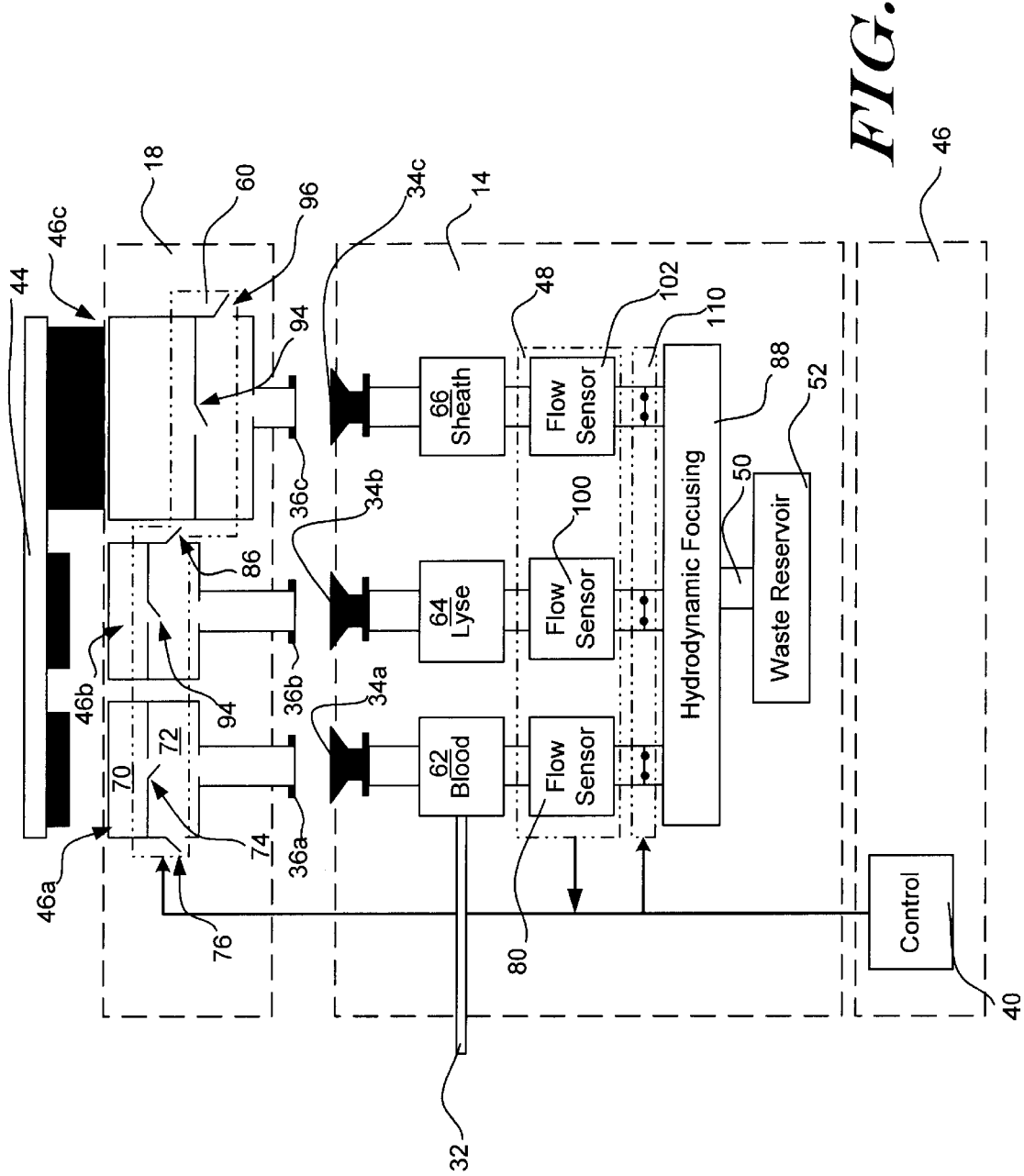
FIG. 3 is a more detailed schematic diagram showing the portable cytometer of FIG. 2 with the cover not yet depressed.
Figure 4:
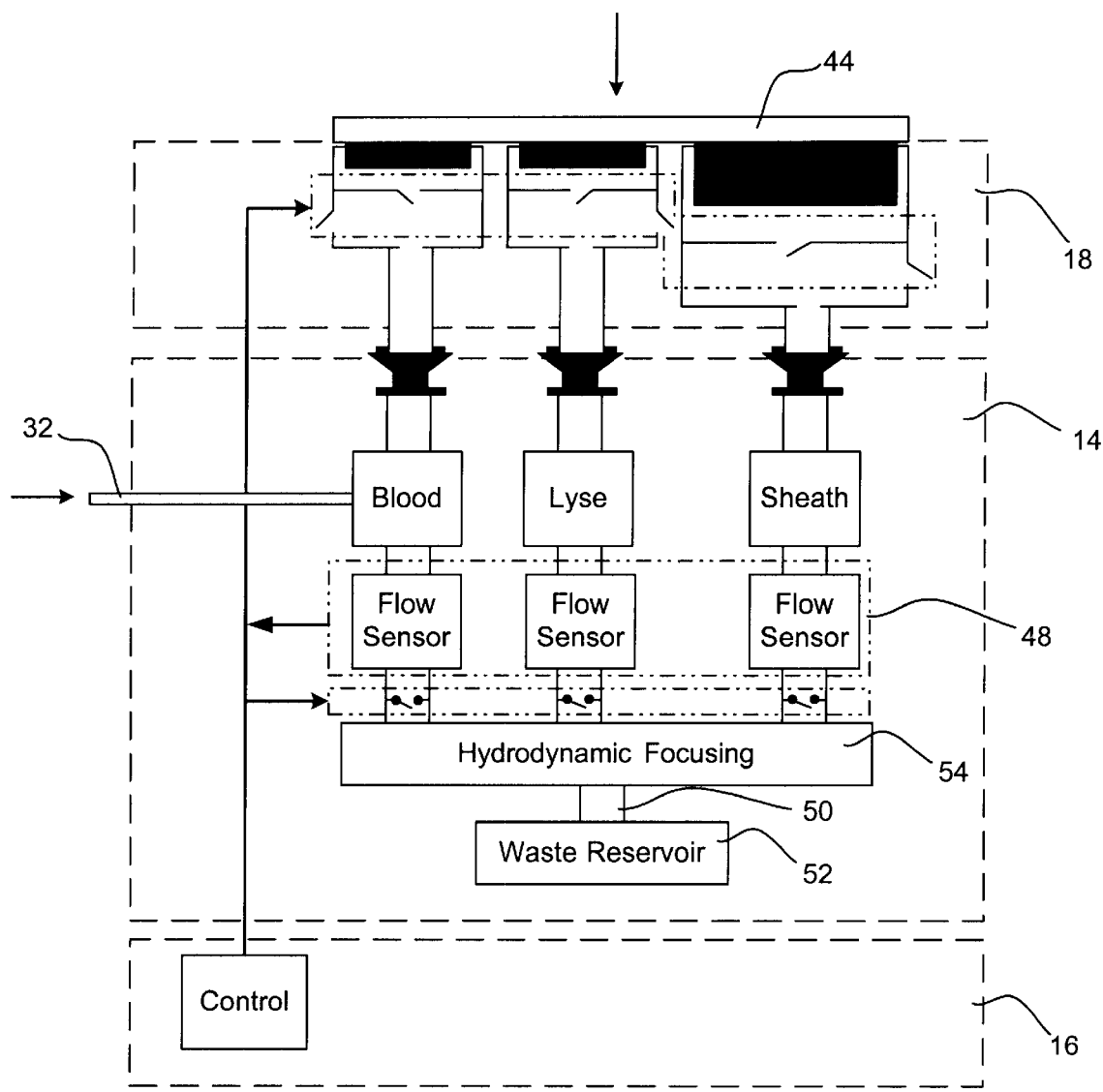
FIG. 4 is a more detailed schematic diagram showing the portable cytometer of FIG. 2 with the cover depressed.

FIG. 3 is a more detailed schematic diagram showing the portable cytometer of FIG. 2 with the cover 18 not yet depressed. FIG. 4 is a more detailed schematic diagram showing the portable cytometer of FIG. 2 with the cover depressed. The cover 18 is shown having a manual pressurizing element 44, pressure-chambers 46a, 46b and 46c, and control microvalves generally shown at 60. The array of light sources and detectors are not shown in these Figures.

There are three pressure chambers 46a, 46b and 46c, one for each fluid to be pressurized. In the illustrative embodiment, pressure chamber 46a provides pressure to a blood sample reservoir 62, pressure chamber 46b provides pressure to a lyse reservoir 64, and pressure chamber 46c provides pressure to a sheath reservoir 66. The size and shape of each pressure chamber 46a, 46b and 46c may be tailored to provide the desired pressure characteristics to the corresponding fluid.

Pressure chamber 46a includes a first pressure chamber 70 and a second pressure chamber 72. A first valve 74 is provided between the first pressure chamber 70 and the second pressure chamber 72 for controllably releasing the pressure in the first pressure chamber 70 to a second pressure chamber 72. A second valve 76, in fluid communication with the second pressure chamber 72, controllably vents the pressure in the second pressure chamber 72. Each valve is preferably an array of electrostatically actuated microvalves that are individually addressable and controllable, as described in, for example, co-pending U.S. patent application Ser. No. 09/404,560, entitled "ADDRESSABLE VALVE ARRAYS FOR PROPORTIONAL PRESSURE OR FLOW CONTROL", and incorporated herein by reference. Pressure chambers 46b and 46c include similar valves to control the pressures applied to the lyse reservoir 64 and sheath reservoir 66, respectively. Alternatively, each valve may be an array of electrostatically actuated microvalves that are pulse modulated with a controllable duty cycle to achieve a controlled "effective" flow or leak rate.

The removable cartridge 14 has pressure receiving ports 34a, 34b, and 34c for receiving the controlled pressures from the cover 18. The controlled pressures are provided to the blood reservoir 62, lyse reservoir 64 and sheath reservoir 66, as shown. The lyse reservoir 64 and sheath reservoir 66 are preferably filled before the removable cartridge 14 is shipped for use, while the blood reservoir 62 is filled from sample collector port 32. A blood sample may be provided to the sample collector port 32, and through capillary action, the blood sample is sucked into the blood reservoir 62. Once the blood sample is in the blood reservoir 62, the cover 18 may be closed and the system may be pressurized.

A flow sensor is provided in-line with each fluid prior to hydrodynamic focussing. Each flow sensor 80, 100 and 102 measures the velocity of the corresponding fluid. The flow sensors are preferably thermal anemometer type flow sensors, and more preferably microbridge type flow sensor.

Microbridge flow sensors are described in, for example, U.S. Pat. Nos. 4,478,076, 4,478,077, 4,501,144, 4,651,564, and 5,050429, all of which are incorporated herein by reference. An output signal from each flow sensor 80, 100 and 102 is provided to controller or processor 40.

The controller or processor 40 opens the first valve 74 when the velocity of the blood sample drops below a first predetermined value and opens the second valve 76 when the velocity of the blood sample increases above a second predetermined value. Valves 84, 86, 94 and 96 operate in a similar manner to control the velocities of the lyse and sheath fluids.

During operation, and to pressurize the system, the manual pressurizing element 44 is depressed. In the example shown, the manual pressurizing element 44 includes three plungers, with each plunger received within a corresponding one of the first pressure chambers. The plungers create a relatively high non-precision pressure in the first pressure chambers. Lower, controlled pressures are built in the secondary chambers by opening the first valves 70, 84 and 94, which produce a controllable leak into the secondary chambers. If too much pressure builds up in the secondary pressure chambers, the corresponding vent valve 76, 86 and 96 are opened to relieve the pressure.

When closing the cover 18, the normally open first valves 74, 84 and 94 are closed while the vent valves 76, 86 and 96 are open. When a predetermined pressure P is achieved in the first pressure chambers, the vent valves 76, 86 and 96 are closed, and the first valves 74, 84 and 94 are opened to build a lower pressure P' in the secondary pressure chambers. The controlled pressure in the secondary pressure chambers provide the necessary pressures to the fluidic circuit of the removable cartridge 14 to produce fluid flow for the blood, lyse and sheath. The velocity of the fluid flow is then measured by the downstream flow sensors 80, 100 and 102. Each flow sensor provides an output signal that is used by the controller or processor 40 to control the operation of the corresponding first valve and vent valve to provide a desired and constant flow rate for each fluid.

Downstream valves generally shown at 110 may also be provided. Controller or processor 40 may close downstream valves 110 until the system is pressurized. This may help prevent the blood, lyse and sheath from flowing into the fluid circuit before the circuit is pressurized. In another embodiment, downstream valves 110 are opened by mechanical action when the cover is closed.

Figure 5:
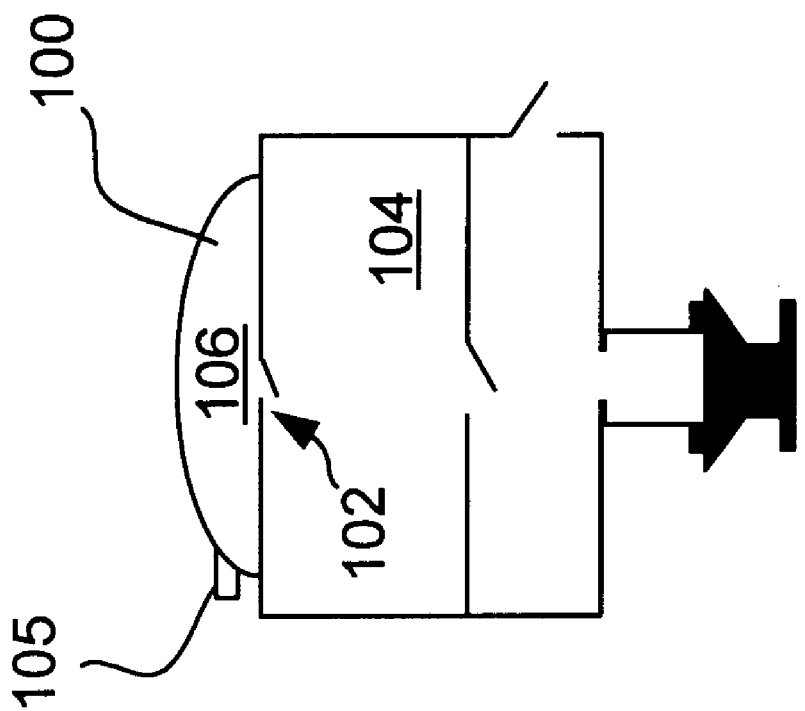
FIG. 5 is a schematic diagram showing an illustrative manual fluid driver having a bulb and check valve.

FIG. 5 is a schematic diagram showing an illustrative manual fluid driver having a bulb 100 and check valve 102. The check valve 102 is preferably a one way valve that allows air in but not out of the first pressure chamber 104. When the bulb 100 is depressed, the air in the interior 106 of the bulb 100 is forced through the check valve 102 and into the first pressure chamber 104. Preferably, another a one-way vent valve 105 is provided that allows air in from the atmosphere but not out of the interior 106 of the bulb 100. Thus, when the bulb is released, the one-way vent valve 105 may allow replacement air to flow into bulb 100.

Rather than using a manually operated fluid driver, it is contemplated that any relatively small pressure source may be used including, for example, an electrostatically actuated meso-pump. One such meso-pump is described in, for example, U.S. Pat. No. 5,836,750 to Cabuz, which is incorporated herein by reference.

Figure 6:
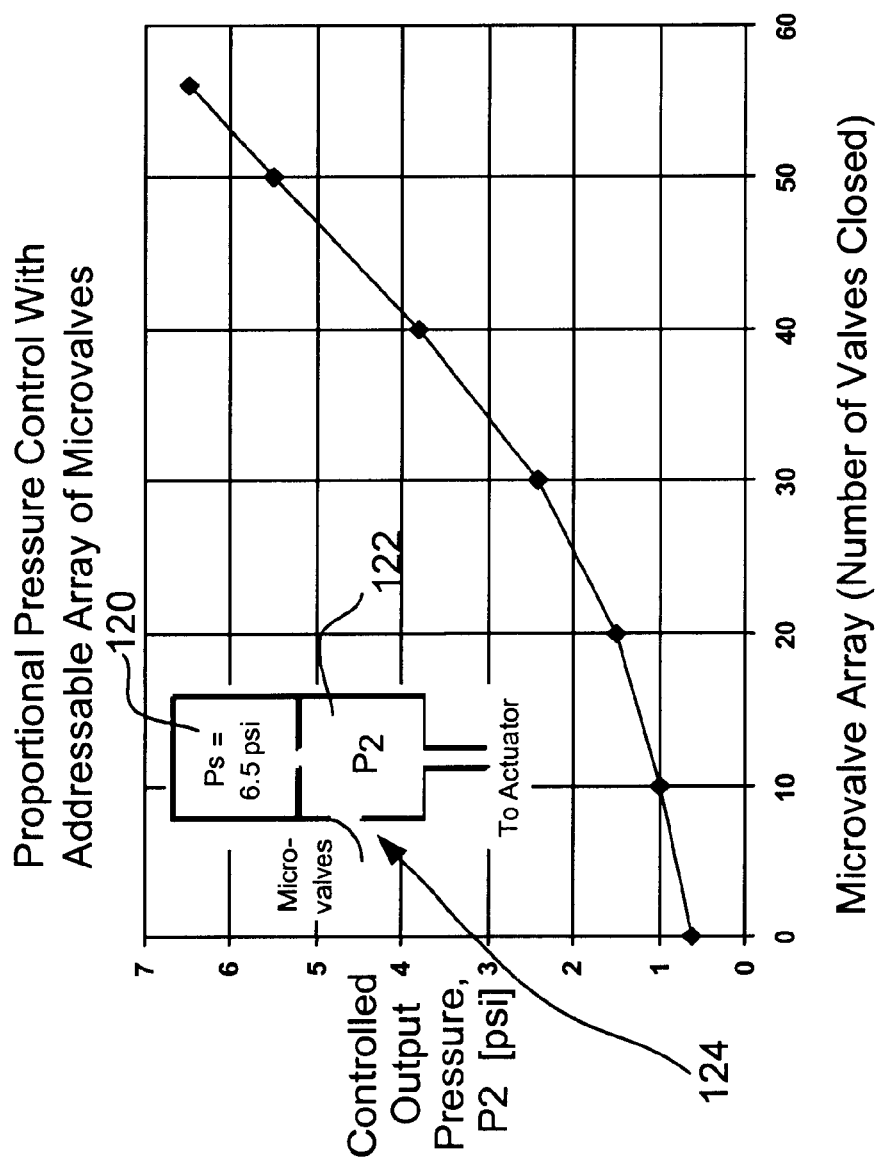
FIG. 6 is a graph showing proportional pressure control of an addressable array of microvalves.

FIG. 6 is a graph showing proportional pressure control produced by a 8×7 addressable array of microvalves. To create the graph shown in FIG. 6, 6.5 psi was applied to a first pressure chamber 120. A small opening was provided to a second pressure chamber 122. The microvalves are shown at 124, and vent the pressure in the second pressure chamber 122. By changing the number of addressable microvalves that are closed, the pressure in the second pressure chamber can be changed and controlled. In the graph shown, the pressure in the second pressure chamber 122 could be changed from about 0.6 psi, when zero of the 8×7 array of microvalves closed, to about 6.5 psi, when all of the 8×7 array of microvalves are closed. These low power, micromachined silicon microvalves can be used for controlling pressures up to 10 psi and beyond.

FIG. 7 is a schematic diagram showing the formation of a flow stream and core by the hydrodynamic focusing block 88 of FIG. 3. The hydrodynamic focusing block 88 receives blood, lyse and sheath at controlled velocities from the fluid driver. The blood is mixed with the lyse, causing the red blood cells to be removed. This is often referred to as red cell lysing. The remaining white blood cells are provided down a central lumen 150, which is surrounded by sheath fluid to produce a flow stream 50. The flow stream 50 includes a core stream 160 surrounded by the sheath fluid 152. The dimensions of the channel are reduced as shown so that the white blood cells 154 and 156 are in single file. The velocity of the sheath fluid is preferably about 9 times that of the core stream 160. However, the velocity of the sheath fluid and core stream 160 remain sufficiently low to maintain laminar flow in the flow channel.

Light emitters 22 and associated optics are preferably provided adjacent one side of the flow stream 50. Light detectors 24 and associated optics are provided on another side of the flow stream 50 for receiving the light from the light emitters 22 via the flow stream 50. The output signals from the light detectors 24 are provided to controller or processor 40, wherein they are analyzed to identify and/or count selected white blood cells in the core stream 160.

Figure 8:
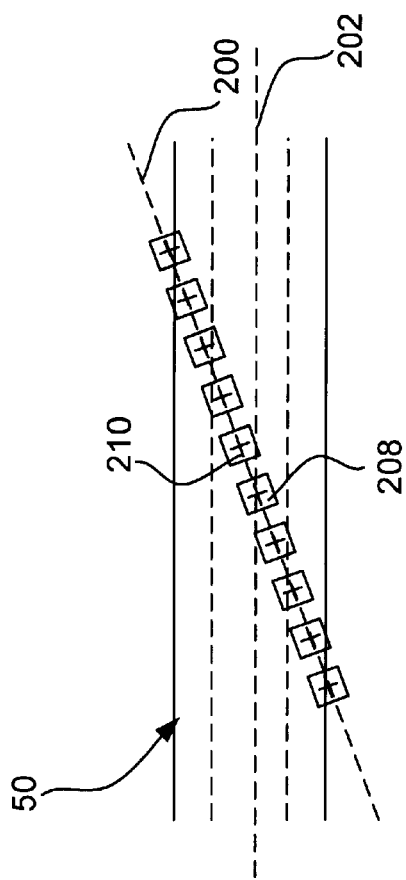
FIG. 8 is a schematic diagram showing an array of light sources and an array of light detectors for analysis of the core stream 160 of FIG. 7.

FIG. 8 is a schematic diagram showing an array of light sources and an array of light detectors for analysis of the core stream 160 of FIG. 7. The light sources are shown as "+" signs and the detectors are shown at boxes. In the embodiment shown, the array of light sources is provided adjacent one side of the flow stream 50, and the array of light detectors is provided adjacent the opposite side of the flow stream. Each of the light detectors is preferably aligned with a corresponding one of the light sources. The array of light sources and the array of light detectors are shown arranged along a light source axis 200 that is slightly rotated relative to the axis 202 of the flow stream 50.

The array of light sources is preferably an array of lasers such as Vertical Cavity Surface Emitting Lasers (VCSEL) fabricated on a common substrate. Because of their vertical emission, VCSELs are ideally suited for packaging in compact instruments such as a portable cytometer. Preferably, the VCSELs are "red" VCSELs that operate at wavelengths that are less than the conventional 850 nm, and more preferably in the 670 nm to 780 nm range. Red VCSELs may have a wavelength, power and polarization characteristic that is ideally suited for scatter measurements.

Some prior art cytometer bench models use a single 9 mW edge-emitting laser with a wavelength of 650 nm. The beam is focussed to a 10×100 micron elongated shape to cover the uncertainty in particle position due to misalignment and width of the core stream. In contrast, the output power of the red VCSELs of the present invention, operating at 670 nm, is typically around 1 mW for a 10 ×10 micron emitter and 100-micron spacing. Thus, the total intensity of the light from a linear array of ten red VCSELs may be essentially the same as that of some prior art bench models.

Using a linear array of lasers oriented at an angle with respect to the flow axis 202 offers a number of important advantages over the single light source configuration of the prior art. For example, a linear array of lasers may be used in determining the lateral alignment of the path of the particles in the core steam. One source of uncertainty in the alignment of the particle stream is the width of the core flow, which leads to statistical fluctuations in the particle path position. These fluctuations can be determined from analysis of the detector data and can be used by the controller or processor 40 to adjust the valves of the fluid driver in order to change the relative pressures that are applied to the sample fluid and the supporting fluids to change the alignment of the selected particles in the flow stream.

To determine the lateral alignment of the cells in the fluid stream 50, the cells pass through several focussed spots produced by the linear array of VCSELs. The cells produce a drop in signal in the corresponding in-line reference detectors. The relative strengths of the signals are used by the controller or processor 40 to determine the center of the particle path and a measure of the particle width.

Figure 9:
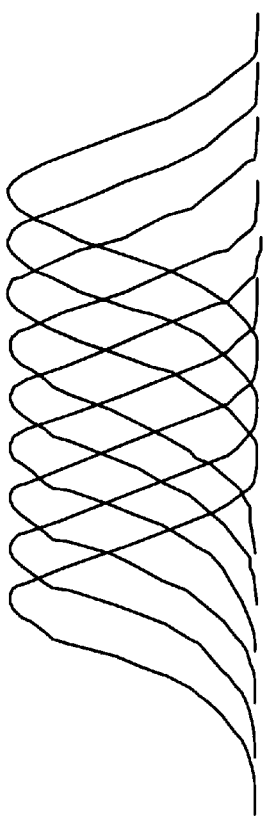
FIG. 9 is a graph showing the light intensity produced along the light source axis of FIG. 8.

For determining particle path and size, the lasers are preferably focussed to a series of Gaussian spots (intensity on the order of 1000 W/cm$^2$) in the plane of the core flow. The spots are preferably about the same size as a white blood cell (10–12 µm). Illustrative Gaussian spots are shown in FIG. 9. Arrays of detectors and their focussing optics are provided on the opposite side of the fluid stream. Lenses with fairly large F-numbers are used to provide a working space of several hundred microns for the cytometer section of the removable cartridge.

Another advantage of using a linear array of lasers rather than a single laser configuration is that the velocity of each cell may be determined. Particle velocity can be an important parameter in estimating the particle size from light scatter signals. In conventional cytometry, the particle velocity is extrapolated from the pump flow rates. A limitation of this approach is that the pumps must be very precise, the tolerance of the cytometer flow chambers must be tightly controlled, no fluid failures such as leaks can occur, and no obstructions such as microbubbles can be introduced to disturb the flow or core formation.

To determine the velocity of each cell, the system may measure the time required for each cell to pass between two adjacent or successive spots. For example, and with reference to FIG. 8, a cell may pass detector 208 and then detector 210. By measuring the time required for the cell to travel from detector 208 to detector 210, and by knowing the distance from detector 208 to detector 210, the controller or processor 40 can calculate the velocity of the cell. This would be an approximate velocity measurement. This is often referred to as a time-of-flight measurement. Once the velocity is known, the time of travel through the spot on which the particle is centered (a few microseconds) may provide a measure of particle length and size.

It is contemplated that the particle velocity can also be used to help control the fluid driver. To reduce the size, cost and complexity of the present invention, the replaceable cartridge of FIG. 1 may be manufactured from a plastic laminate or molded parts. While such manufacturing techniques may provide inexpensive parts, they are typically less dimensionally precise and repeatable, with asymmetrical dimensions and wider tolerance cross-sections. These wider tolerances may produce variations in particle velocity, particularly from cartridge to cartridge. To help compensate for these wider tolerances, the time-of-flight measurement discussed above can be used by the controller or processor 40 to adjust the controlled pressures applied to the blood, lyse and sheath fluid streams such that the particles in the core stream have a relatively constant velocity.

To further evaluate the cell size, it is contemplated that laser beams may be focused both along the cell path and across the cell path. Additionally, multiple samples across the cell may be analyzed for texture features, to correlate morphological features to other cell types. This may provide multiple parameters about cell size that may help separate cell types from one another.

Another advantage of using a linear array of lasers rather than a single layer configuration is that a relatively constant light illumination may be provided across the flow channel. This is accomplished by overlapping the Gaussian beams from adjacent VCSELs, as shown in FIG. 9. In prior art single laser systems, the light illumination across the flow channel typically varies across the channel. Thus, if a particle is not in the center of the flow channel, the accuracy of subsequent measurements may be diminished.

Figure 10:
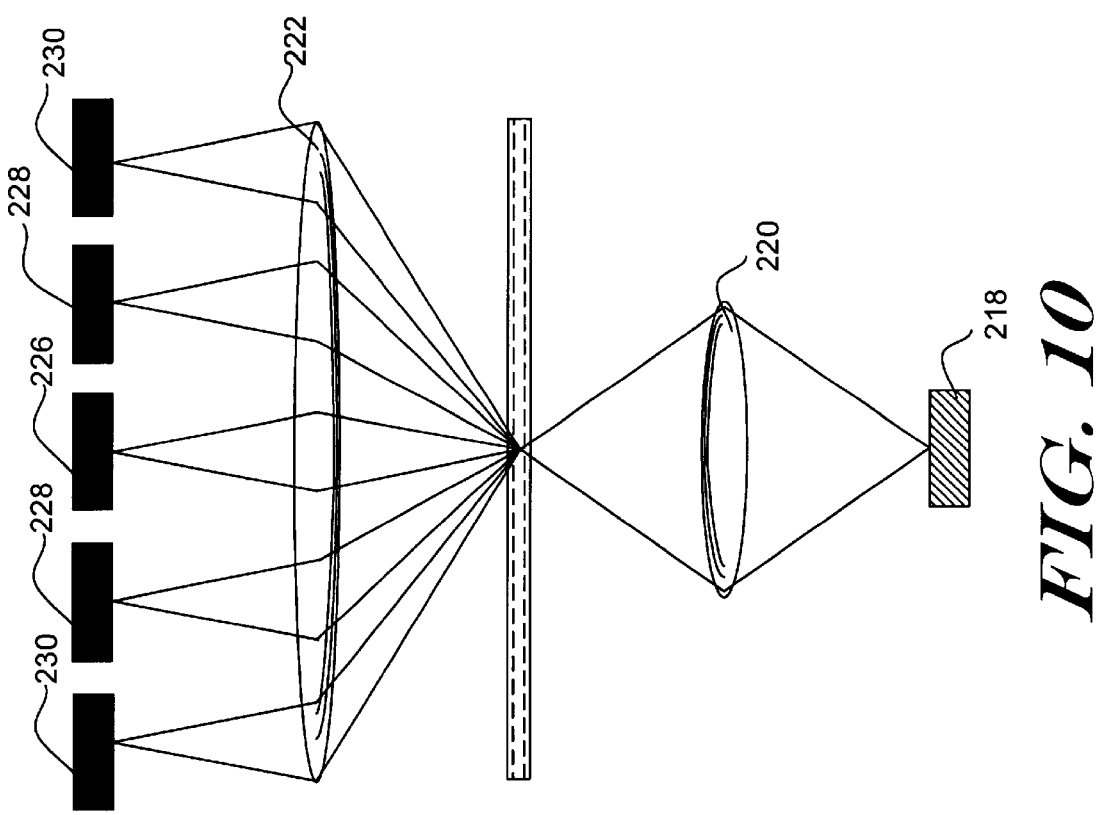
FIG. 10 is a schematic diagram showing an illustrative light source and detector pair of FIG. 8.

To perform the above described measurements, each detector in FIG. 8 may be a single in-line detector. To measure FALS and SALS scatter, however, each detector may further include two annular detectors disposed around the in-line detector, as shown in FIG. 10. Referring to FIG. 10, a VCSEL 218 is shown providing light in an upward direction. The light is provided through a lens 220, which focuses the light to a Gaussian spot in the plane of the core flow. Lens 220 may be a microlens or the like, which is either separate from or integrated with the VCSEL 218. The light passes through the core flow, and is received by another lens 222, such as a diffractive optical element. Lens 222 provides the light to in-line detector 226 and annular detectors 228 and 230. The in-line detector 226 detects the light that is not significantly scattered by the particles in the core stream. Annular detector 228 detects the forward scatter (FALS) light, and annular detector 230 detects the small angle scatter (SALS) light.

Figure 11:
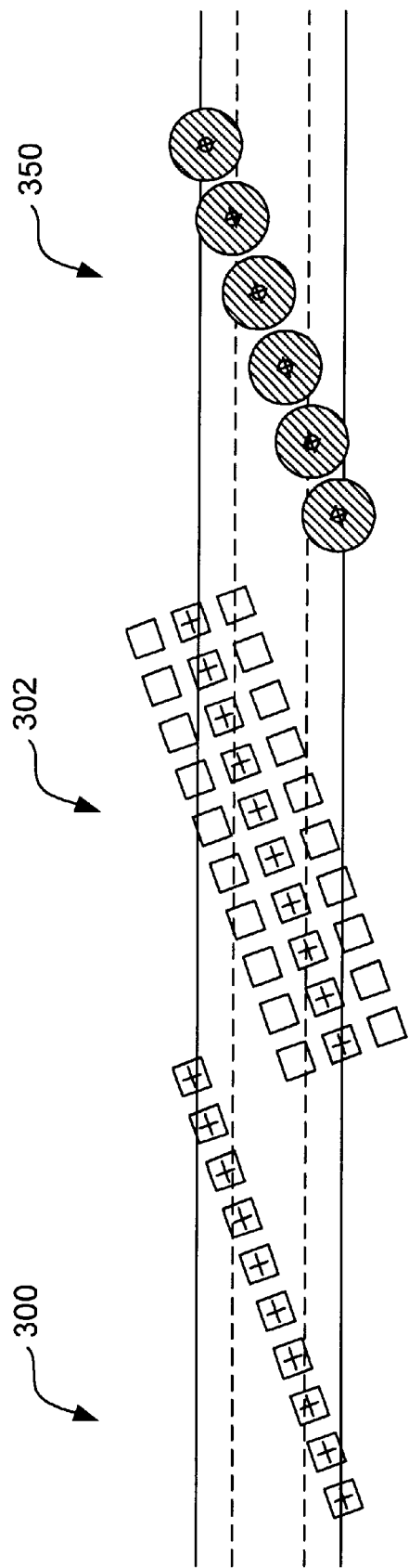
FIG. 11 is a schematic diagram showing three separate arrays of light sources and detectors, each positioned along a different light source axis that is slightly rotated relative to the central flow axis of the flow stream of FIG. 7.

FIG. 11 shows another illustrative embodiment of the present invention that includes three separate arrays of light sources and light detectors. Each array of light sources and light detectors are positioned along a different light source axis that is slightly rotated relative to the central flow axis of the flow stream. By using three arrays, the optics associated with each array may be optimized for a particular application or function. For detecting small angle scattering (SALS), laser light that is well-focussed on the plane of the core flow is desirable. For detecting forward scattering (FALS), collimated light is desirable.

Referring specifically to FIG. 11, a first array of light sources and light detectors is shown at 300. The light sources and light detectors are arranged in a linear array along a first light source axis. The first light source axis is rotated relative to the flow axis of the flow stream. The light sources and light detectors may be similar to that described above with respect to FIG. 8, and preferably are used to measure, for example, the lateral alignment of the cells in the flow stream, the particle size, and the velocity of the particles.

FIG. 12 is a schematic diagram showing an illustrative light source and detector pair of the first array 300 shown in FIG. 11. A VCSEL 302 is shown providing light in an upward direction. The light is provided through a lens 304, which focuses the light to a Gaussian spot in the plane of the core flow. The light passes through the core flow, and is received by another lens 306. Lens 306 provides the light to in-line detector 308. The in-line detector 308 detects the light that is not significantly scattered by the particles in the core stream.

A second array of light sources and light detectors is shown at 310. The light sources are arranged in a linear array along a second light source axis that is rotated relative to the flow axis of the flow stream. The light detectors include three linear arrays of light detectors. One array of light detectors is positioned in line with the linear array of light sources. The other two linear arrays of light detectors are placed on either side of the in-line array of light detectors, and are used for measuring the small angle scattering (SALS) produced by selected particles in the flow stream.

FIG. 13 is a schematic diagram showing an illustrative light source and corresponding detectors of the second array shown in FIG. 11. A VCSEL 320 is shown providing light in an upward direction. The light is provided through a lens 322, which focuses the light to a Gaussian spot in the plane of the core flow. The light passes through the core flow, and is received by another lens 324, such as a diffractive optical element (DOE) 324. Lens 324 provides the light to the in-line detector 326 and the two corresponding light detectors 328 and 330 placed on either side of the in-line light detector 326.

The in-line detector 326 may be used to detect the light that is not significantly scattered by the particles in the core stream. Thus, the in-line linear array of light detectors of the second array 302 may be used to provide the same measurements as the in-line array of detectors of the first array 300. The measurements of both in-line arrays of detectors may be compared or combined to provide a more accurate result. Alternatively, or in addition, the in-line detectors of the second array 302 may be used as a redundant set of detectors to improve the reliability of the cytometer.

It is contemplated that the in-line detectors of the second array 302 may also be used in conjunction with the in-line detectors of the first array 300 to more accurately determine the time-of-flight or velocity of the particles in the flow stream. The measurement may be more accurate because the distance between detectors may be greater. As indicated above, by knowing the velocity of the particles, small variations in the flow rate caused by the fluid driver can be minimized or removed by the controller.

Light detectors 328 and 330 of FIG. 13 are used to measure the small angle scattering (SALS) produced by selected particles in the flow stream. The light detectors 328 and 330 are therefore preferably spaced sufficiently from the in-line detector 326 to intercept the small angle scattering (SALS) produced by selected particles in the flow stream.

Referring back to FIG. 11, a third array of light sources and light detectors 350 is preferably provided to measure the forward angle scattering (FALS) produced by selected particles in the flow stream. The light sources are arranged in a linear array along a third light source axis that is rotated relative to the flow axis of the flow stream. Each light source preferably has a corresponding light detector, and each light detector is preferably annular shaped with a non-sensitive region or a separate in-line detector in the middle. The annular shaped light detectors are preferably sized to intercept and detect the forward angle scattering (FALS) produced by selected particles in the flow stream.

Figure 14:
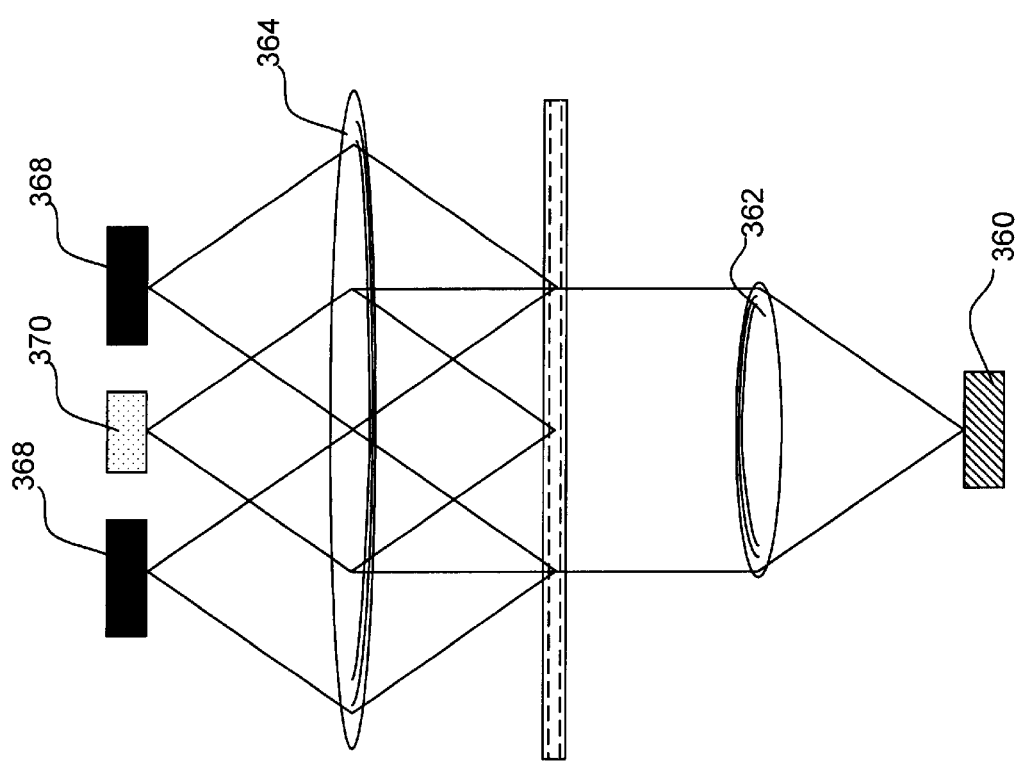
FIG. 14 is a schematic diagram showing an illustrative light source and detector pair of the third array shown in FIG. 11.

FIG. 14 is a schematic diagram showing an illustrative light source and detector pair of the third array of light sources and light detectors 350 shown in FIG. 11. A VCSEL 360 is shown providing light in an upward direction. The light is provided through a lens 362 such as a collimating lens, which provides substantially collimated light to the core flow. As indicated above, collimated light is desirable for detecting forward scattering (FALS) light. The light passes through the core flow, and is received by another lens 364. Lens 364 provides the received light to the annular shaped detector 368.

The annular shaped detector 378 is preferably sized to intercept and detect the forward angle scattering (FALS) produced by selected particles in the flow stream. A non-sensitive region or a separate in-line detector 370 may be provided in the middle of the annular shaped detector 368. If a separate in-line detector 370 is provided, it can be used to provide the same measurement as the in-line detectors of the first array 300 and/or second array 302. When so provided, the measurements from all three in-line arrays of detectors of first array 300, second array 302 and third array 350 may be compared or combined to provide an even more accurate result. The in-line detectors of the third array 302 may also be used as another level of redundancy to improve the reliability of the cytometer.

It is contemplated that the in-line detectors of the third array 350 may also be used in conjunction with the in-line detectors if the first array 300 and/or second array 302 to more accurately determine the time-of-flight or velocity of the particles in the flow stream. The measurement may be more accurate because the distance between detectors may be greater. As indicated above, by knowing the velocity of the particles, small variations in the flow rate caused by the fluid driver can be minimized or removed by the controller.

By using three separate arrays of light sources and detectors, the optics associated with each array can be optimized for the desired application. As can be seen, the optics associated with the first array 300 are designed to provide well-focussed laser light on the plane of the core flow. This helps provide resolution to the alignment, size and particle velocity measurements performed by the first array 300. Likewise, the optics associated with the second array 302 are designed to provide well-focussed laser light on the plane of the core flow. Well focussed light is desirable when measuring the small angle scattering (SALS) produced by selected particles in the flow stream. Finally, the optics associated with the third array 350 are designed to provide collimated light to the core flow. As indicated above, collimated light is desirable when measuring forward angle scattering (FALS) produced by selected particles in the flow stream.

Figure 15:
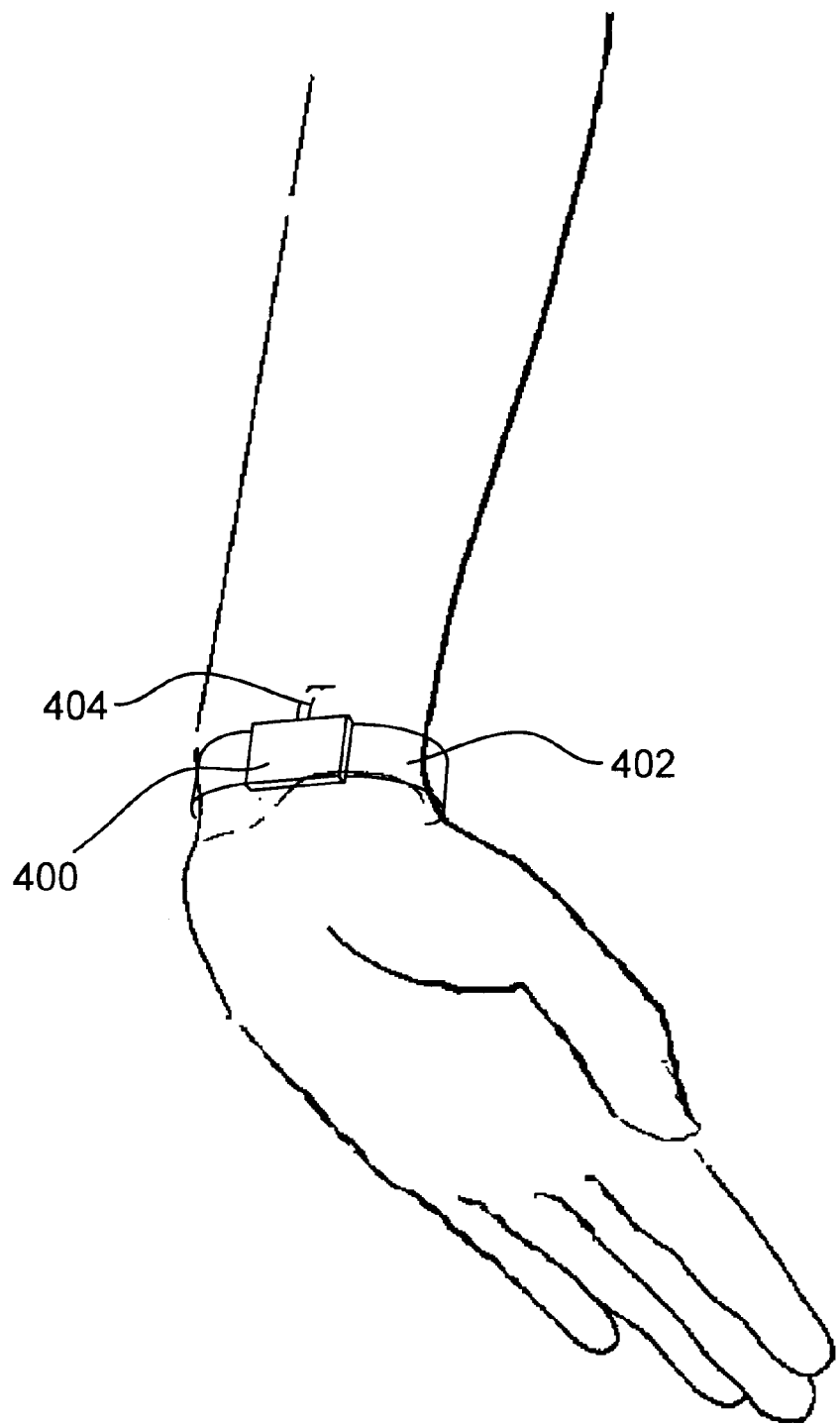
FIG. 15 is a perspective view of an illustrative embodiment of the portable cytometer of the present invention adapted to be worn around the wrist.

FIG. 15 is a perspective view of an illustrative embodiment of the portable cytometer of the present invention adapted to be worn around the wrist. The portable cytometer is shown at 400, and may be similar to that shown in FIG. 1. A band 402 secures the portable cytometer 400 to the wrist of a user.

As indicated above, the user may obtain a removable cartridge and provide a blood sample to the sample collector port 32 (see FIG. 1) of the removable cartridge. The blood sample may be collected by, for example, a finger prick. The user may then insert the removable cartridge into the housing, and manually pressurize the system. The portable cytometer may then provide a reading that indicates if the user should seek medical treatment. The reading may be a visual reading, an audible sound or any other suitable indicator.

Rather than obtaining the blood sample by a finger prick or the like, it is contemplated that a catheter 404 or the like may be inserted into a vein of the user and attached to the sample collector port 32. This may allow the system to automatically collect a blood sample from the user whenever a reading is desired. Alternatively, it is contemplated that the portable cytometer may be implanted in the user, with the sample collector port 32 connected to a suitable blood supply.

Having thus described the preferred embodiments of the present invention, those of skill in the art will readily appreciate that the teachings found herein may be applied to yet other embodiments within the scope of the claims hereto attached.

What is claimed is:

1. An optical detection system for analyzing predetermined characteristics of a flow stream, the flow stream having a central axis along the direction of flow, the optical detection system comprising:
   two or more light sources positioned on a common axis at an angle relative to the central axis of the flow stream for providing light through different parts of the flow stream;
   light receiving means for receiving the light from the two or more light sources, and for providing at least one signal in response thereto; and
   processing means for receiving the at least one signal from the light receiving means and for using the at least one signal for analyzing the predetermined characteristics of the flow scream.

2. An optical detection system according to claim 1, wherein the two or more light sources are positioned along a light source axis that is offset relative to the central axis of flow of the flow stream.

3. An optical detection system according to claim 1, wherein the two or more spaced light sources are part of an array of VCSEL devices.

4. An optical detection system according to claim 3, wherein the VCSEL devices operate in the red spectrum.

5. An optical detection system according to claim 1, wherein each of the two or more light sources have a corresponding lens.

6. An optical detection system according to claim 5, wherein each lens is an integrated micro lens.

7. An optical detection system according to claim 5, wherein selected lenses focus the light at a central plane that includes the central axis of the flow stream.

8. An optical detection system according to claim 7, wherein the light that is focused at the central plane is used for detecting the small angle scattering (SALS) produced by one or more particles in the flow stream.

9. An optical detection system according to claim 8, wherein the one or more particles include white blood cells.

10. An optical detection system according to claim 9, wherein the white blood cells include neutrophils and/or lymphocytes white blood cells.

11. An optical detection system according to claim 7, wherein the light that is focused at the central plane is used for determining the velocity of one or more particles in the flow stream.

12. An optical detection system according to claim 7, wherein the light that is focused at the central plane is used for determining the size of one or more particles in the flow stream.

13. An optical detection system according to claim 5, wherein selected lenses provide substantially collimated light through the flow stream.

14. An optical detection system according to claim 13, wherein the substantially collimated light is used for detecting the forward angle scattering (FALS) produced by one or more particles in the flow stream.

15. An optical detection system according to claim 14, wherein the one or more particles include white blood cells.

16. An optical detection system according to claim 15, wherein the white blood cells include neutrophils and/or lymphocytes white blood cells.

17. An optical detection system according to claim 1, wherein the two or more light sources include a first set of light sources positioned along a first light source axis that is rotated relative to the central axis of the flow stream, light from the first set of light sources is focused at a central plane that includes the central axis of the flow stream.

18. A method for determining the alignment of one or more particles in a flow stream relative to a central axis of the flow stream, the method comprising:

activating two or more light sources positioned laterally across the central axis of the flow stream to provide light through different parts of the flow stream;

monitoring an output response of two or more detectors that receive the light from the two or more light sources;

detecting a change in the response of one or more of the detectors when a particle passes between the detector and the corresponding light source; and determining the alignment of the one or more particles in the flow stream relative to the central axis of the flow stream by noting which detector or detectors produced a change in response.

19. A method for determining the velocity of one or more particles in a flow stream, the flow stream having a width and a length, the length extending from an upstream position to a downstream position, the method comprising the steps of:

activating at least one upstream light source at the upstream position of the flow stream to provide light through the flow stream;

monitoring an output response of at least one upstream detector that receives the light from the upstream light source;

activating at least one downstream light source at a downstream position of the flow stream, a downstream light source positioned at a different position along the width of the flow stream than an upstream light source to provide light through a different part of the flow stream;

monitoring an output response of at least one downstream detector that receives the light from the downstream light source;

detecting a change in the response of the at least one upstream detector when a particle passes between the at least one upstream detector and the at least one upstream light source;

detecting a change in the response of the at least one downstream detector when the same particle passes between the at least one downstream detector and the at least one downstream light source; and determining a time lag between the change in response of the at least one upstream detector and the change in response of the at least one downstream detector, the time lag being related to the speed of the particle.

20. A method for determining the small angle scattering (SALS) produced by one or more particles in a flow stream, the method comprising:

activating two or more light sources positioned on a common axis at an angle relative to the flow stream to provide light through different parts of the flow stream;

focusing the light provided by the two or more light sources at the flow stream;

receiving the light from the two or more light sources using at least one detector, each detector having a detector region laterally spaced from an in-line position of the corresponding light source; and determining the SALS produced by the one or more particles by examining the response of the at least one detector.

21. A method according to claim 20 wherein each detector has at least two detector regions for each of the light sources, one positioned in one direction relative to an in-line position of the corresponding light source and another positioned in another direction relative to the in-line position of the corresponding light source.

22. A method for determining the forward angle scattering (FALS) produced by one or more particles in a flow stream, the method comprising:

activating two or more light sources laterally positioned across the flow stream to provide light through the flow stream;

collimating the light provided by the two or more light sources at the flow stream;

receiving the light from the two or more light sources using at least one detector, each detector having a detector region laterally spaced from an in-line position of the corresponding light source; and determining the FALS produced by the one or more particles by examining the response of the at least one detector.

23. A method according to claim 22, wherein each of the at least one detectors is annular in shape.

24. An optical detection system for analyzing predetermined characteristics of a flow stream, the flow stream having a central axis along the direction of flow, the optical detection system comprising:

a linear array of light sources for providing light through different parts of the flow stream, the linear array of light sources oriented at an angle with respect to the central axis of the flow stream;

a linear array of light detectors for receiving the light from the linear array of light sources, and for providing at least one signal in response thereto; and processing means for receiving the at least one signal from the linear array of light detectors and for using the at least one signal for analyzing the predetermined characteristics of the flow stream.

25. An optical detection system for analyzing predetermined characteristics of a flow stream, the flow stream having a central axis along the direction of flow, the optical detection system comprising:

two or more light sources positioned laterally across the central axis of the flow stream for providing light through different parts of the flow stream;

light receiving means for receiving the light from the two or more light sources, and for providing at least one signal in response thereto; and processing means for receiving the at least one signal from the light receiving means and for using the at least one signal for analyzing the predetermined characteristics of the flow stream; and wherein the two or more light sources are positioned along a light source axis that is offset relative to the central axis of flow of the flow stream.

26. An optical detection system according to claim 25, wherein the two or more light sources collectively provide substantially constant light intensity across the flow stream.

27. An optical detection system for analyzing predetermined characteristics of a flow stream, the flow stream having a central axis along the direction of flow, the optical detection system comprising:

two or more light sources positioned laterally across the central axis of the flow stream for providing light through different parts of the flow stream;

light receiving means for receiving the light from the two or more light sources, and for providing at least one signal in response thereto; and processing means for receiving the at least one signal from the light receiving means and for using the at least one signal for analyzing the predetermined characteristics of the flow stream; and wherein the two or more light sources include a first set of light sources positioned along a first light source axis that is rotated relative to the central axis of the flow stream, light from the first set of light sources is focused at a central plane that includes the central axis of the flow stream.

28. An optical detection system according to claim 27, wherein the light receiving means includes a first set of light detectors for receiving light from the first set of light sources after the light passes through the flow stream, each of the first set of light detectors having a corresponding lens that focuses the light substantially on the corresponding light detector.

29. An optical detection system according to claim 28, wherein the first set of light sources and the first set of light detectors are used to detect the alignment of the flow of one or more particles relative to the central axis of the flow stream.

30. An optical detection system according to claim 28, wherein the first set of light sources and the first set of light detectors are used to detect the speed of one or more particles in the flow stream.

31. An optical detection system according to claim 28, wherein the first set of light sources and the first set of light detectors are used to detect the size of one or more particles in the flow stream.

32. An optical detection system according to claim 27, wherein the two or more light sources include a second set of light sources positioned along a second light source axis that is rotated relative to the central axis of the flow stream and offset from the first light source axis, each of the second set of light sources having a corresponding lens that focuses the light at a central plane that includes the central axis of the flow stream.

33. An optical detection system according to claim 32, wherein the light receiving means includes a second set of light detectors, each of the second set of light detectors having a detector region laterally spaced from an in-line position of the corresponding light source.

34. An optical detection system according to claim 33, wherein each of the second set of light detectors has at least two detector regions for each of the second set of light sources, one positioned in one direction relative to an in-line position of the corresponding light source and another positioned in another direction relative to the in-line position of the corresponding light source, each of the second set of light detectors having a corresponding lens that focuses the light substantially on the corresponding light detector.

35. An optical detection system according to claim 34, wherein the second set of light detectors are used to detect the small angle scattering (SALS) produced by one or more particles in the flow stream.

36. An optical detection system according to claim 34, wherein the second set of light detectors include a third detector in-line with the corresponding light source, the third detector used in conjunction with the first set of detectors to detect the speed of one or more particles in the flow stream.

37. An optical detection system according to claim 33, wherein the two or more light sources include a third set of light sources positioned along a third light source axis that is rotated relative to the central axis of the flow stream, each of the third set of light sources having a corresponding lens that provides substantially collimated light through the flow stream.

38. An optical detection system according to claim 37, wherein the light receiving means includes a third set of light detectors positioned in line with the third set of light sources, each of the third set of light detectors having a corresponding lens that focuses the substantially collimated light substantially on the corresponding light detector.

39. An optical detection system according to claim 38, wherein each of the third set of light detectors are annular in shape.

40. An optical detection system according to claim 39, wherein the third set of light sources and the third set of annular light detectors are used to detect the forward angle scattering (FALS) produced by the selected particles in the flow stream.

41. A method for determining the small angle scattering (SALS) produced by one or more particles in a flow stream, the method comprising:

activating two or more light sources positioned laterally across the flow stream to provide light through different parts of the flow stream;

focusing the light provided by the two or more light sources at the flow stream;

receiving the light from the two or more light sources using at least one detector, each detector having a detector region laterally spaced from an in-line position of the corresponding light source; and determining the SALS produced by the one or more particles by examining the response of the at least one detector; and wherein each detector has at least two detector regions for each of the light sources, one positioned in one direction relative to an in-line position of the corresponding light source and another positioned in another direction relative to the in-line position of the corresponding light source.

42. An optical detection system for analyzing predetermined characteristics of a flow stream, the flow stream having a central axis along the direction of flow, the optical detection system comprising:

two or more light sources positioned laterally across the central axis of the flow stream for providing light through different parts of the flow stream;

light receiving means for receiving the light from the two or more light sources, and for providing at least one signal in response thereto; and processing means for receiving the at least one signal from the light receiving means and for using the at least one signal for analyzing the predetermined characteristics of the flow stream; and wherein the two or more light sources, having overlapping Gaussian beams, collectively provide substantially constant light intensity across the flow stream.

43. An optical detection system for analyzing predetermined characteristics of a flow stream, the flow stream having a central axis along the direction of flow, the optical detection system comprising:

two or more light sources positioned laterally across the central axis of the flow stream for providing light through different parts of the flow stream;

light receiving means for receiving the light from the two or more light sources, and for providing at least one signal in response thereto; and processing means for receiving the at least one signal from the light receiving means and for using the at least one signal for analyzing the predetermined characteristics of the flow stream; and wherein the two or more light sources are positioned along an axis that is offset relative to the central axis of flow of the flow stream.

* * * * *